United States Patent
Freed (10) Patent No.: US 10,327,442 B2
(45) Date of Patent: Jun. 25, 2019

(54) APPARATUS FOR MAINTENANCE OF HARVESTED HEARTS FOR TRANSPLANTING

(71) Applicant: TEVOSOL, INC., Edmonton (CA)

(72) Inventor: Darren Freed, Edmonton (CA)

(73) Assignee: TEVOSOL, INC., Edmonton (CA)

( * ) Notice: Subject to any disclaimer, the term of this patent is extended or adjusted under 35 U.S.C. 154(b) by 131 days.

(21) Appl. No.: 15/128,634

(22) PCT Filed: Mar. 18, 2015

(86) PCT No.: PCT/CA2015/050201
§ 371 (c)(1),
(2) Date: Sep. 23, 2016

(87) PCT Pub. No.: WO2015/143552
PCT Pub. Date: Oct. 1, 2015

(65) Prior Publication Data
US 2017/0223950 A1    Aug. 10, 2017

Related U.S. Application Data

(60) Provisional application No. 61/970,532, filed on Mar. 26, 2014.

(51) Int. Cl.
*A01N 1/02*    (2006.01)
*A61N 1/39*    (2006.01)
(Continued)

(52) U.S. Cl.
CPC ......... *A01N 1/0247* (2013.01); *A01N 1/0252* (2013.01); *A01N 1/0273* (2013.01);
(Continued)

(58) Field of Classification Search
CPC .. A01N 1/0247; A01N 1/0252; A61B 5/0402; A61N 1/3625; A61N 1/3968
See application file for complete search history.

(56) References Cited

U.S. PATENT DOCUMENTS

| 5,157,930 A | 10/1992 | McGhee et al. |
| 5,217,860 A * | 6/1993 | Fahy .................. A01N 1/02 |
| | | 435/1.2 |

(Continued)

FOREIGN PATENT DOCUMENTS

| CA | 2144952 A1 | 3/1994 |
| CA | 2521324 A1 | 10/2004 |

(Continued)

OTHER PUBLICATIONS

International Preliminary Report on Patentability dated Sep. 27, 2016 in PCT/CA2015/050201.

(Continued)

*Primary Examiner* — Benjamin R Whatley (57) ABSTRACT

An apparatus, a system, and methods for maintaining and monitoring an excized donor heart. The apparatus comprises a first component for receiving and submerging therein an excized heart in a constantly circulating perfusate solution and a second component comprising equipment for adjusting the temperature and oxygen content of the perfusate solution. The first component comprises an integral pair of defibrillating pads. A first conduit infrastructure interconnects the first module, the second module and an aorta of the excized donor heart pushing a perfusion solution from the first module through the second module into the aorta. The second conduit infrastructure connects the first module with the right atrium and the left atrium for pushing the perfusion solution from the first module into the atria. The third conduit infrastructure connects the first module with the pulmonary artery and provides an after pressure to the flow of the perfusion solution from the pulmonary artery.

6 Claims, 3 Drawing Sheets

(51) Int. Cl.
*A61N 1/362* (2006.01)
*A61B 5/0402* (2006.01)

(52) U.S. Cl.
CPC ......... *A61N 1/3622* (2013.01); *A61N 1/3625* (2013.01); *A61N 1/3968* (2013.01); *A61B 5/0402* (2013.01)

(56) References Cited

U.S. PATENT DOCUMENTS

| | | | |
|---|---|---|---|
| 5,716,378 A * | 2/1998 | Minten | A01N 1/02 607/3 |
| 5,807,737 A | 9/1998 | Schill et al. | |
| 6,046,046 A | 4/2000 | Hassanein | |
| 6,582,375 B2 | 6/2003 | Melvin et al. | |
| 6,953,655 B1 | 10/2005 | Hassanein et al. | |
| 7,045,279 B1 | 5/2006 | Laske et al. | |
| 7,811,808 B2 | 10/2010 | Van Der Plaats et al. | |
| 8,585,380 B2 | 11/2013 | Hassanein et al. | |
| 9,706,768 B2 * | 7/2017 | Freed | A01N 1/0247 |
| 2001/0018569 A1 | 8/2001 | Erbel et al. | |
| 2004/0248281 A1 | 12/2004 | Wright et al. | |
| 2005/0255442 A1 | 11/2005 | Brassil et al. | |
| 2006/0154358 A1 | 7/2006 | Hassanein et al. | |
| 2007/0009881 A1 | 1/2007 | Arzt et al. | |
| 2007/0098694 A1 | 5/2007 | Khuri et al. | |
| 2010/0028850 A1 | 2/2010 | Brassil | |
| 2011/0129810 A1 | 6/2011 | Owen et al. | |
| 2011/0177487 A1 | 7/2011 | Simsir et al. | |
| 2012/0183945 A1 | 7/2012 | Steen | |
| 2012/0282591 A1 | 11/2012 | Thatte et al. | |
| 2013/0157248 A1 | 6/2013 | Fishman et al. | |
| 2013/0295552 A1 | 11/2013 | Hassanein et al. | |
| 2014/0220550 A1 | 8/2014 | Van Der Plaats et al. | |
| 2015/0017710 A1 * | 1/2015 | Freed | A01N 1/0247 435/284.1 |
| 2016/0113269 A1 * | 4/2016 | Woodard | A01N 1/0263 435/284.1 |

FOREIGN PATENT DOCUMENTS

| | | |
|---|---|---|
| CA | 2861545 A1 | 7/2013 |
| DE | 102005048625 A1 | 4/2007 |
| EP | 2809153 | 12/2014 |
| EP | 3229588 | 10/2017 |
| WO | 2013106908 A1 | 7/2013 |
| WO | 2015143552 A1 | 1/2015 |

OTHER PUBLICATIONS

Office Action dated Apr. 4, 2016 in related Canadian Patent Application No. 2,861,545.
Supplementary European Search Report dated Jan. 25, 2016 in EP Patent Application No. 13738530.
International Preliminary Report on Patentability dated Apr. 23, 2014 in PCT/CA2013/000031.
International Search Report dated Jun. 8, 2015 in PCT/CA2015/050201.
De Hart, et al., "An ex vivo platform to simulate cardiac physiology: a new dimension for therapy development and assessment", The International Journal of Artificial Organs, Jun. 2011, pp. 495-505, vol. 34, No. 6.
Tipton, et al., "The use of Langendorff preparation to study the bradycardia of training", Medicine and Science in Sports, vol. 9, No. 4, pp. 220-230 (1977).
International Search Report received in PCT Application No. PCT/CA2013/000031 dated Apr. 15, 2013.
Written Opinion received in PCT Application No. PCT/CA2013/000031 dated Apr. 15, 2013.
Written Opinion received in PCT/CA2015/050201 dated Jun. 8, 2015.
Non-final Office Action dated Jan. 8, 2016 in related U.S. Appl. No. 14/372,909.
Final Office Action dated Jul. 12, 2016 in related U.S. Appl. No. 14/372,909.
Non-final Office Action dated Jan. 20, 2017 in related U.S. Appl. No. 14/372,909.
Notice of Allowance dated Apr. 11, 2017 in related U.S. Appl. No. 14/372,909.
Written Opinion dated Mar. 15, 2016 in PCT/CA2015/051316.
International Search Report dated Mar. 16, 2016 in PCT/CA2015/051316.
International Preliminary Report on Patentability (IPRP) dated Apr. 10, 2017 in PCT/CA2015/051316.
Muhlbacher et al., "Preservation solutions for transplantation", Transplant Proc., 1999, vol. 31(5), pp. 2069-2070.
Communication from European Patent Office in related EP Patent Application No. 13738530.8 dated Nov. 21, 2017.
Extended European Search Report dated Nov. 30, 2017 in EP Patent Application No. 15767752.7.
Examination Report No. 1 dated Apr. 27, 2018 in related Australian Patent Application No. 2015234580.
Search Report dated Sep. 3, 2018 in related EP Patent Application No. 15867786.4.

* cited by examiner

FIG. 3

APPARATUS FOR MAINTENANCE OF HARVESTED HEARTS FOR TRANSPLANTING

CROSS-REFERENCE TO RELATED APPLICATION

This application is a national filing of International Application No. PCT/CA2015/050201, filed on Mar. 18, 2015, entitled "Apparatus for Maintenance of Harvested Hearts for Transplanting," having as inventor Darren Freed, which claims benefit of U.S. Provisional Application No. 61/970,532, filed on Mar. 26, 2014.

FIELD OF THE INVENTION

The present invention pertains to apparatus, systems, and methods for ex vivo perfusion and maintenance of harvested donor hearts, and more particularly, to pre-transplant assessment of harvested donor hearts for their suitability for transplantation.

BACKGROUND OF THE INVENTION

Heart failure affects 10% of North Americans and is the leading hospital discharge diagnosis. The diagnosis of heart failure is accompanied by a survival outlook that is comparable to a major cancer. There are limited rehabilitation options available to patients who are suffering with heart failure, and few strategies actually re-power the heart. Cardiac transplantation remains the gold-standard therapeutic intervention for patients with end-stage heart failure, with an increasing number of individuals being added to the transplant wait list every year. However, wider application of this life-preserving intervention is limited by the availability of donors. Data from the International Society of Heart and Lung Transplantation Registry shows that cardiac transplantation is in progressive decline in suitable donors (2007, *Overall Heart and Adult Heart Transplantation Statistics*). Two hundred and fifty eight Canadians have died during the last decade (2000-2010; Heart and Stroke Foundation of Canada) while waiting for heart transplantation. Similarly, in the United States, 304 patients died in 2010 alone while waiting for heart transplantation (Organ Procurement and Transplantation Network, US Dept. of Health & Human Services). This phenomenon is primarily due to a shortage of suitable organ donors, and is being experienced across the globe.

Time is of the essence for removal of a heart from a donor and its successful transplantation into a recipient. The following principles generally apply for optimal donor heart preservation for the period of time between removal from the donor and transplantation: (i) minimization of cell swelling and edema, (ii) prevention of intracellular acidosis, (iii) prevention of injury caused by oxygen free radicals, and (iv) provision of substrate for regeneration of high-energy phosphate compounds and ATP during reperfusion. The two main sources of donor hearts for transplantation are breathing patients who have suffered irreversible loss of brain function as a result of blunt head trauma or intracerebral hemorrhage and are classified as "brainstem-dead" donors, and patients who have suffered circulatory death and are referred to as "non-heart-beating" donors.

Brainstem-dead organ donors can be maintained under artificial respiration for extended periods of time to provide relative hemodynamic stability up throughout their bodies until the point of organ retrieval. Therefore, cardiac perfusion is uncompromised and organ functionality is theoretically maintained. However, brainstem death itself can profoundly affect cardiac function. The humoral response to brainstem death is characterized by a marked rise in circulating catecholamines. Physiological responses to this "catecholamine storm" include vasoconstriction, hypertension and tachycardia, all of which increase myocardial oxygen demand. In the coronary circulation Significant increased levels of catecholamine circulating throughout the vascular system induce vasoconstriction which in turn, compromises myocardial oxygen supply and can lead to subendocardial ischemia. This imbalance between myocardial oxygen supply and demand is one factor implicated in the impairment of cardiac function observed following brainstem death (Halejcio-Delophont et al., 1998, *Increase in myocardial interstitial adenosine and net lactate production in brain-dead pigs: an in vivo microdialysis study*. Transplantation 66(10):1278-1284; Halejcio-Delophont et al., 1998, *Consequences of brain death on coronary blood flow and myocardial metabolism*. Transplant Proc. 30(6):2840-2841). Structural myocardial damage occurring after brainstem death is characterized by myocytolysis, contraction band necrosis, sub-endocardial hemorrhage, edema and interstitial mononuclear cell infiltration (Baroldi et al., 1997, *Type and extent of myocardial injury related to brain damage and its significance in heart transplantation: a morphometric study*. J. Heart Lung Transplant 16(10):994-1000). In spite of no direct cardiac insult, brainstem-dead donors often exhibit reduced cardiac function and the current views are that only 25% of hearts can be recovered from this donor population for transplantation.

Well-defined criteria have been developed for harvesting organs for transplantation from non-heart-beating donors (Kootstra et al., 1995, *Categories of non-heart-beating donors*. Transplant Proc. 27(5):2893-2894; Bos, 2005, *Ethical and legal issues in non-heart-beating organ donation*. Transplantation, 2005. 79(9): p. 1143-1147). Non-heart-beating donors have minimal brain function but do not meet the criteria for brainstem death and therefore, cannot be legally declared brainstem dead. When it is clear that there is no hope for meaningful recovery of the patient, the physicians and family must be in agreement to withdraw supportive measures. Up to this point in care, non-heart-beating patients are often supported with mechanical ventilation as well as intravenous inotropic or vasopressor medication. However, only those with single system organ failure (neurologic system) can be considered for organ donation. Withdrawal of life support, most commonly the cessation of mechanical ventilation, is followed by anoxic cardiac arrest after which, the patient must remain asystolic for five minutes before organ procurement is allowed. Consequently, non-heart-beating donors are necessarily exposed to variable periods of warm ischemia after cardiac arrest which may result in various degrees of organ damage. However, provided that the time duration of warm ischemia is not excessive, many types organs, i.e., kidneys, livers, and lungs, harvested from non-heart-beating donors are able to recover function after transplantation with success rates that approximate those for transplanted organs from brainstem-dead beating donors.

Numerous perfusion apparatus, systems and methods have been developed for ex vivo maintenance and transportation of harvested organs. Most employ hypothermic conditions to reduce organ metabolism, lower organ energy requirements, delay the depletion of high energy phosphate reserves, delay the accumulation of lactic acid, and retard morphological and functional deteriorations associated with disruption of oxygenated blood supply. Harvested organs are generally perfused in these systems with preservative solutions comprising antioxidants and pyruvate under low temperatures to maintain their physiological functionality. However, it has been found that increasing amounts of free radicals and catalytic enzymes are produced during extended maintenance of harvested organs in pulsing pressurized hypothermic systems. Fluctuating perfusion pressures in such systems can damage the organs by washing off their vascular endothelial lining and traumatize the underlying tissues. Furthermore, the harvested organs will elute increasing amounts of intracellular, endothelial and membrane constituents resulting in their further physiological debilitation.

The short-comings of hypothermic apparatus, systems and methods have been recognized by those skilled in these arts, and alternative apparatus, systems and methods have been developed for preservation and maintenance of harvested organs at temperatures in the range of about 25° C. to about 35° C., commonly referred to as "normothermic" temperatures. Normothermic systems typically use perfusates based on the Viaspan formulation supplemented with one or more of serum albumin as a source of protein and colloid, trace elements to potentiate viability and cellular function, pyruvate and adenosine for oxidative phosphorylation support, transferrin as an attachment factor; insulin and sugars for metabolic support, glutathione to scavenge toxic free radicals as well as a source of impermeant, cyclodextrin as a source of impermeant, scavenger, and potentiator of cell attachment and growth factors, a high $Mg^{++}$ concentration for microvessel metabolism support, mucopolysaccharides for growth factor potentiation and hemostasis, and endothelial growth factors (Viaspan comprises potassium lactobionate, $KH_2PO_4$, $MgSO_4$, raffinose, adenosine, glutathione, allopurinol, and hydroxyethyl starch). Other normothermic perfusion solutions have been developed and used (Muhlbacher et al., 1999, *Preservation solutions for transplantation*. Transplant Proc. 31(5):2069-2070). While harvested kidneys and livers can be maintained beyond twelve hours in normothermic systems, it has become apparent that normothermic bathing, and maintenance of harvested hearts by pulsed perfusion beyond 12 hours results in deterioration and irreversible debilitation of the hearts' physiological functionality. Another disadvantage of using normothermic continuous pulsed perfusion systems for maintenance of harvested hearts is the time required to excise the heart from a donor, mount it into the nomothermic perfusion system and then initiate and stabilize the perfusion process. After the excised heart has been stabilized, its physiological functionality is determined and if transplantation criteria are met, then the excised heart is transported as quickly as possible to a transplant facility.

Current technologies employ occlusive roller pumps to provide flow of perfusate into an isolated aortic root. With this approach, the heart cannot eject against the pump without a significant rise in systolic stress. Furthermore, there currently is no device in the market that allows comprehensive assessment of right and left ventricular systolic and diastolic function, in addition to providing metabolic assessments of excised hearts.

SUMMARY OF THE INVENTION

The present disclosure pertains to an apparatus, a system, and methods for maintenance and monitoring of the physiological functionality of an excised donor heart.

The apparatus comprises a first component for receiving and submerging an excised heart in a constantly circulating perfusate solution, a second component comprising equipment for adjusting the temperature and oxygen content of the perfusate solution, a third component comprising a non-occlusive centrifugal pump to pump perfusate into an isolated aortic root of an excised heart during preservation mode and to provide non-occlusive resistance to ejection (afterload) during working/assessment mode, and a fourth component comprising a non-occlusive centrifugal pump to provide filling of the excised heart (preload) during working/assessment mode. By positioning the pumps below the heart, coupled with the non-occlusive nature of the pumps, decompression of the excised heart is provided in the event of poor cardiac function or arrhythmias. The need for gravity as an energy source for provision of preload or afterload to excised hearts is obviated in the current design, thus permitting a compact, portable design for the apparatus of the present disclosure.

The system generally comprises the apparatus into which an excised heart is installed, wherein the apparatus is interconnected with: (i) a perfusate pumping system, (ii) flow sensors for monitoring the flow of perfusate to and from the installed heart's aorta, pulmonary artery, pulmonary vein, and vena cava, (iii) an ECG apparatus interconnectable with the excised heart, and (vv) probes interconnecting the installed heart with instruments for monitoring the excised heart's physiological functionality using load independent indices and load dependent indices.

BRIEF DESCRIPTION OF THE DRAWINGS

The present invention will be described in conjunction with reference to the following drawings in which.

DESCRIPTION OF THE INVENTION

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "about" or "approximately" means within 20%, preferably within 10%, and more preferably within 5% of a given value or range.

The term "modulate" as used herein means to regulate the operation of a device by increasing a signal to the device in order to increase an output by the device, or by decreasing a signal to the device in order to decrease an output by the device The term "afterload" means the mean tension produced by a chamber of the heart in order to contract. It can also be considered as the 'load' that the heart must eject blood against. Afterload is therefore a consequence of aortic large vessel compliance, wave reflection and small vessel resistance (left ventricular afterload) or similar pulmonary artery parameters (right ventricular afterload).

The term "preload" refers to the stretching of a single cardiac myocyte immediately prior to contraction and is therefore related to the sarcomere length. Since sarcomere length cannot be determined in the intact heart, other indices of preload such as ventricular end diastolic volume or pressure are used. As an example, preload increases when venous return is increased.

The term "cardiac myocyte" means a cardiac muscle cell.

The term "stroke volume" (SV) means the volume of blood ejected by the right/left ventricle in a single contraction. It is the difference between the end diastolic volume (EDV) and the end systolic volume (ESV). Mathematically, SV=EDV−ESV. The stroke volume is affected by changes in preload, afterload and inotropy (contractility). In normal hearts, the SV is not strongly influenced by afterload whereas in failing hearts, the SV is highly sensitive to afterload changes.

The term "stroke work" (SW) refers to the work performed by the left or right ventricle to eject the stroke volume into the aorta or pulmonary artery, respectively. The area enclosed by the pressure/volume loop is a measure of the ventricular stroke work, which is a product of the stroke volume and the mean aortic or pulmonary artery pressure (afterload), depending on whether one is considering the left or the right ventricle.

The term "ejection fraction" (EF) means the fraction of end diastolic volume that is ejected out of the ventricle during each contraction. Mathematically, EF=SV/EDV. Healthy ventricles typically have ejection fractions greater than 0.55. Low EF usually indicates systolic dysfunction and severe heart failure can result in EF lower than 0.2. EF is also used as a clinical indicator of the inotropy (contractility) of the heart. Increasing inotropy leads to an increase in EF, while decreasing inotropy decreases EF.

The term "end systolic pressure volume relationship" (ESPVR) describes the maximal pressure that can be developed by the left ventricle at any given left ventricular volume, or alternatively, by the right ventricle at any given right ventricular volume. This implies that the PV loop cannot cross over the line defining ESPVR for any given contractile state. The slope of ESPVR (Ees) represents the end-systolic elastance, which provides an index of myocardial contractility. The ESPVR is relatively insensitive to changes in preload, afterload and heart rate. This makes it an improved index of systolic function over other hemodynamic parameters like ejection fraction, cardiac output and stroke volume. The ESPVR becomes steeper and shifts to the left as inotropy (contractility) increases. The ESPVR becomes flatter and shifts to the right as inotropy decreases.

The term "preload recruitable stroke work relationship" (PRSW) means a measure of cardiac contractility, and is the linear relationship between SW and EDV.

The term "pressure-volume area" (PVA) means the total mechanical energy generated by ventricular contraction. This is equal to the sum of the stroke work (SW), encompassed within the PV loop, and the elastic potential energy (PE). Mathematically, PVA=PE+SW.

The term "Langendorff perfusion" refers to a method of perfusing an excised heart with a nutrient-rich oxygenated solution in a reverse fashion via the aorta. The backwards pressure causes the aortic valve to shut thereby forcing the solution into the coronary vessels, which normally supply the heart tissue with blood. This feeds nutrients and oxygen to the cardiac muscle, allowing it to continue beating for several hours after its removal from the animal.

The term "working heart" as used herein, refers to clinical ex vivo coronary perfusion throughout a excised heart by ventricular filling via the left atrium and ejection from the left ventricle via the aorta driven by the heart's contractile function and regular cardiac rhythm. The excised heart is attached by cannulae to a perfusate reservoir and circulatory pumps in a Langendoff preparation. The flow of perfusate through the excised heart in "working heart" mode is in the direction opposite to the flow of perfusate during Langedorff perfusion.

The term "ischemia" means a condition that occurs when blood flow and oxygen are kept from the heart.

The term "conduit" as used herein means tubing and/or cannula.

The present disclosure pertains to apparatus, systems and methods for maintaining an excised heart under continuous Langendorff perfusion until transplantation. The apparatus and systems are communicable and cooperable with cardiac monitoring equipment and microprocessors for monitoring the physiological condition and functioning of the excised heart.

One embodiment of the present disclosure pertains to an exemplary modular apparatus for receiving and maintaining an excised heart under continuous Langendorff perfusion until transplantation. The exemplary apparatus comprises two modules. The first module comprises a hard-shell reservoir, also referred to herein as a reservoir, for housing therein an excised heart under constant bathing with a suitable perfusate solution. The excised heart is mounted onto a stand and submerged within the hard-shell reservoir. The hard-shell reservoir is provided with four ports (i.e., two egress ports and two ingress ports) that are sealingly engageable by conduits that have been interconnected to the excised heart's right atrium, left atrium, aorta, and pulmonary artery. The second module is a perfusate conditioning apparatus comprising: (i) a heat-exchanger for warming and maintaining the perfusate solution at a user-specified temperature (typically referred to as a normothermic temperature), and (ii) and oxygenator for maintaining the dissolved oxygen levels in the perfusate solution above 95% saturation, and maintaining the pH balance through addition of carbon dioxide. The two modules are interconnected by a conduit infrastructure that is engageable by a pump such as those exemplified by centrifugal pumps. Suitable centrifugal pumps are exemplified by ROTAFLOW® centrifugal pumps (ROTAFLOW is a registered trademark of Maquet Cardiopulmonary AG Corp., Hirrlingen, Fed. Rep. Ger.), by Medtronic's centrifugal blood BIO-PUMP®s BIO-PUMP is a registered trademark of Medtronics Bio-Medicus Inc., Minnetonka, Minn., USA), by Sorin's RevOlution 5 blood pump (Sorin Group USA, Arvada, Colo., USA). In operation, the centrifugal pump provides a constant flow of perfusate solution from the first module (i.e., the hard-shell reservoir) to the second module (i.e., the perfusate conditioning apparatus). The first module is additionally provided with ports for receiving therethrough leads from cardiac monitoring equipment for engaging specific sites on and/or in the excised heart. Each module can be separately assembled and prepared for use multiple units, thereby facilitating rapid assembly and configuration of the apparatus as needed to receive and maintain an excised heart.

Figure 1:
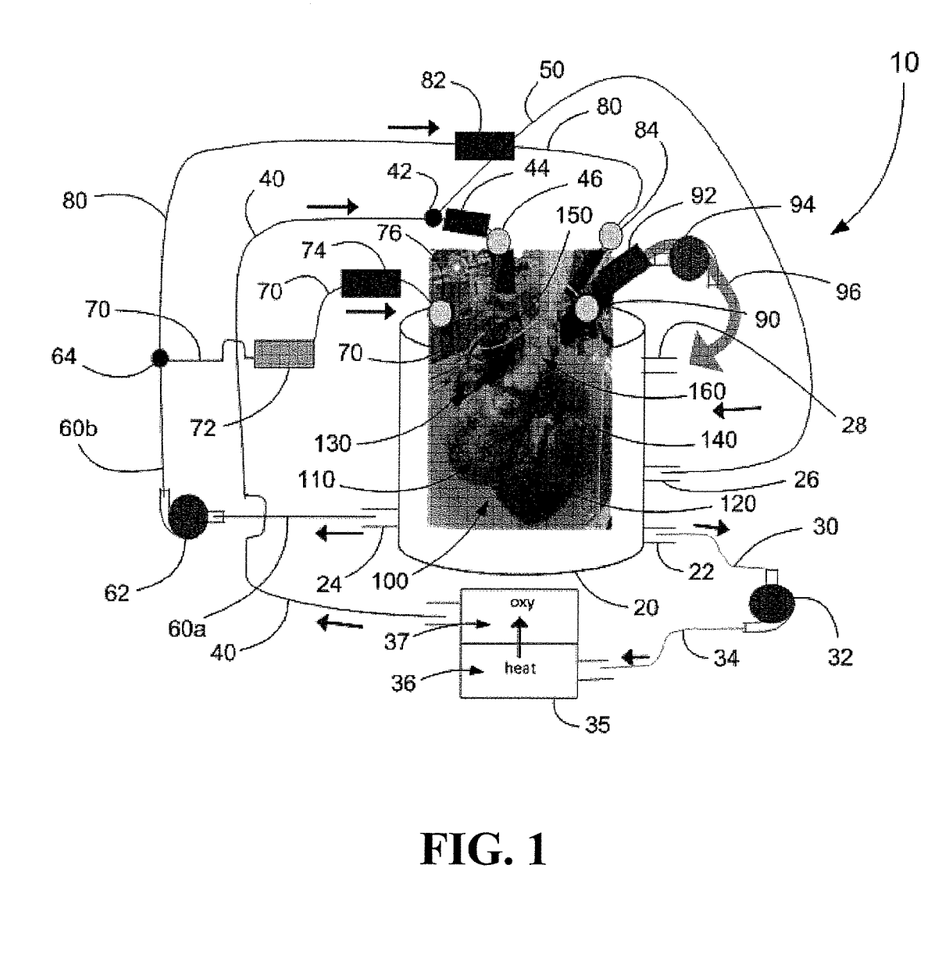
FIG. 1 is a schematic illustration of an exemplary maintenance apparatus for harvested donor hearts, according to one embodiment of the present disclosure.

An exemplary apparatus 10 according to one embodiment of the present disclosure is shown in FIG. 1. The apparatus comprises: (i) a first component which is a hard-shell reservoir 20 housing a removable support (not shown) for mounting thereon and therein an excised heart 100, and (ii) a second component which is a perfusate solution conditioning device 35 comprising a heat-exchanger 36 and an oxygenator 37. The hard-shell reservoir 20 may additionally have a level sensor (not shown) for monitoring the level of perfusate solution in the hard-shell reservoir 20. The two components are interconnected by a first conduit infrastructure comprising: (i) an egress line 30 that is sealably engageable at one end with a port 22 provided therefore near the bottom of the hard-shell reservoir 20 and is sealably engageable at its other end with the inlet of a first centrifugal pump 32. The outlet of the first centrifugal pump 32 is sealably engaged with a line 34 that is sealably engageable with an inlet to the heat exchanger 36 of the perfusate solution conditioning device 35. A line 40 is sealably engageable with an outlet from the oxygenator 37 of the perfusate solution conditioning device 35. The other end of line 40 is sealably engageable with a Y-connector 42 which diverts a portion of the flow of conditioned perfusion solution from the perfusion solution conditioning device 35 into a purge line 50 that is sealably engageable with a first ingress port 26 provided therefore on the hard-shell reservoir 20. The remainder of the flow of perfusate solution conditioning device 35 is diverted by the Y-connector 42 into a flow sensor 44 interconnected with an integrated pressure port 46 that is clampable into the aorta 150 of the harvested heart. In operation, the flow sensor 44 measures aortic flow of the conditioned perfusion solution from the perfusate solution conditioning device 35 into the aorta 150. Perfusion solution egressing from the hard-shell reservoir 20 into the perfusate solution conditioning device 35 is conditioned by heating in the heat exchanger 36 to a normothermic temperature from the range of about 20° C. to about 37° C. and then is oxygenated by oxygenator 37 prior to flowing into line 40 for conveyance into the aorta 150. The diastolic pressure in the aorta 150 can be specified and tightly regulated by computer controlled feedback to modulate the centrifugal pump 32. During assessment mode, with provision of flow into the left atrium the heart ejects the perfusion solution back through line 40 with the centrifugal pump 32 providing resistance (afterload). In this manner the heart can beat against an afterload pressure that is delivered by the flow of perfusate solution from the centrifugal pump 32.

A second conduit infrastructure comprises a line 60a sealably engageable at one end with a second egress port 24 provided therefore near the bottom of the hard-shell reservoir 20, and its other end sealably engageable with the inlet into a second centrifugal pump 62. The outlet of the second centrifugal pump 62 is sealably engageable with a line 60b that terminates in a Y-connector 64. Y-connector 64 splits the pressurized flow of perfusion solution into two lines 70, 80. Line 70 is interconnected with, firstly, an occlusion clamp 72, secondly, a flow sensor 74, and thirdly, an integrated pressure port 76. The terminal end of line 70 is insertable into the right atrium 130 of the harvested heart 100. It should be noted that occlusion clamp 72 is preferably a servo-actuated partial occlusion clamp whose variable positions enables regulation of the rate of flow of the perfusion solution into the right atrium 130 and therefore, can also be used to modulate pressure delivered to the harvested heart 100. Line 80 is interconnected with, firstly, a flow sensor 82, and secondly, an integrated pressure port 84. The terminal end of line 80 is insertable into the left atrium 140 of the harvested heart 100. It should be noted that lines 70, 80 are additionally provided with bubble detectors (not shown). During the assessment mode, pump 62 provides flow of the perfusate solution into the right atrium and left atrium (preload pressure) under a feedback loop from pressure ports 84, 76 with differential control of flow into the right atrium and left atrium being provided by modulation of clamp 72. In the event of overpressurization of the heart as a consequence, for example, of arrhythmia or poor cardiac function, the flow of perfusate solution from pump 62 is decreased thereby allowing decompression of the heart to occur through passive retrograde flow of the perfusate solution back through the pump 62.

A third conduit infrastructure comprises a line 96 that is clampable into the pulmonary artery 160 of the harvested heart 100. The line 96 is sequentially sealably engageable with an integrated pressure port 90, a flow sensor 92, and a third centrifugal pump 94. The terminal end of the line 96 is sealably engageable with the second ingress port 28 provided therefore on the hard-shell reservoir 20. Pump 94 provides resistance (afterload pressure) to the right ventricle, through computer-controlled modulation of the pump 94 in reference to feedback from pressure port 90.

Figure 2:
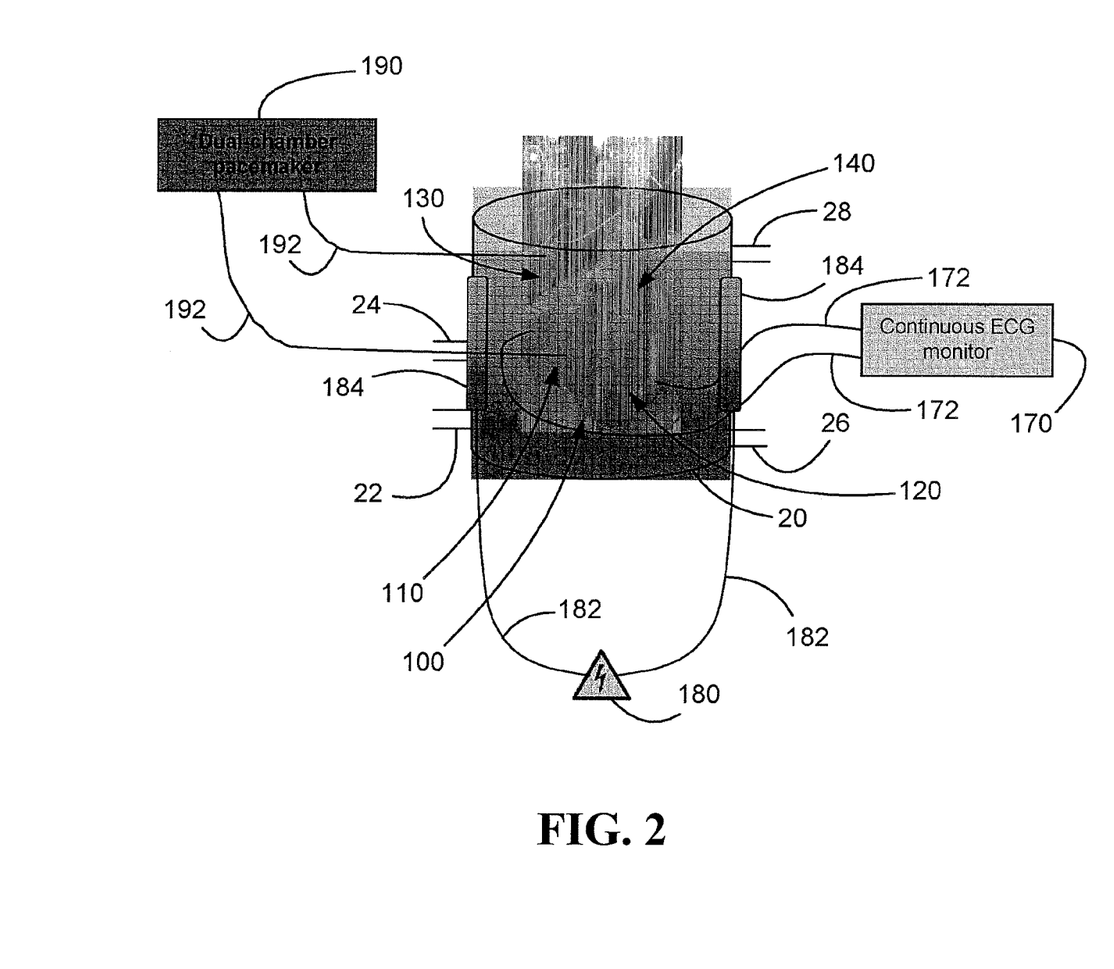
FIG. 2 is a close-up partial view of exemplary embodiments of the pacemaker, ECG monitor, and defibrillator components of the harvested donor heart maintenance apparatus of the present disclosure.

FIG. 2 illustrates exemplary monitoring and maintenance equipment for maintaining a harvested heart in a functional condition during storage and transport in the exemplary apparatus of the present disclosure. Leads 172 from an ECG monitoring device 170 are engageable with, for example, the right ventricle 110 and the left ventricle 120 of a harvested heart 100 for monitoring the electrical activity of the harvested heart 100. Alternatively, the ECG leads may be integrally incorporated into the walls of the hard-shell reservoir 20. Leads 192 from a dual-chamber pacemaker 190 are engageable with the right atrium 130 and the right ventricle 110 of the harvested heart 100. Although a dual-chamber pacemaker is preferable for use with the apparatus 10 of the present disclosure, it is optional to substitute a single-chamber pacemaker having a single lead that is engageable with the right atrium or the right ventricle. Two defibrillator pads 184 are integrally provided opposite each other on the inner surfaces of the hard-shell reservoir 20 and are connected by leads 182 to a defibrillator. The ECG monitoring device 170, the pacemaker 190 and the defibrillator 180 may be mounted on a support provided therefore (not shown) that is an integral component of the hard-shell reservoir 20. Alternatively, the ECG monitoring device 170, the pacemaker 190 and the defibrillator 180 may be integrally incorporated into the housing of a transportation container configured to receive therein the hard-shell reservoir 20.

As soon as an excised heart 100 is mounted onto the removable support and placed into the hard-shell reservoir 20, the terminal end of line 40 is clamped into the aorta, 150, line 70 is inserted into the right atrium 130, line 80 is inserted into the left atrium 140, and line 96 is clamped into the pulmonary artery 160. Then, a suitable perfusion solution exemplified by whole blood, whole blood amended with citrate and/or phosphate and/or dextrose, modified Krebs solutions, Viaspan, modified Viaspan solutions, and the like, is added into the hard-shell reservoir 20 until the heart 100 is completely submerged. It should be noted that the hard-shell reservoir 20 may be additionally provided with a level sensor (not shown) and a supplementary supply of the perfusion solution (not shown) for conveyance into the hard-shell reservoir 20 as need to maintain the excised heart 100 fully submerged during storage and transport in the apparatus of the present disclosure.

When in operation, the pump 32 continuously draws the perfusate solution from the hard-shell reservoir 20 from egress port 22 into line 30 into the perfusate solution conditioning device 35 wherein the perfusate solution is conditioned by warming to a normothermic temperature and then, is oxygenated. The conditioned and pressurized conditioned perfusate solution is then conveyed to Y-connector 42 that diverts a portion of the conditioned perfusate solution into purge line 50 for conveyance through ingress port 26 back into the hard-shell reservoir 20 where it circulates about and baths the heart 100. The remaining flow of pressurized conditioned perfusate solution is conveyed through flow sensor 44 and integrated pressure port 46 into the aorta 150. It is to be noted that the purge line 50 is positioned to be the highest point in the assembled apparatus 10 when an excised heart 100 is mounted therein so that any air that is ejected by the heart immediately goes out via the purge line 50 and back to the hard-shell reservoir 20.

A preload centrifugal pump 62 draws the perfusion solution out of the hard-shell reservoir through egress port 24 into line 60b and then pushes the perfusion solution to Y-connector 64 where its flow is split into two lines 70,80. The perfusion solution is pushed through line 70 through a computer-controlled servo-actuated partial occlusion clamp 72, a flow sensor 74, and an integrated pressure port 76 into the right atrium 130. The variable positions of the servo-actuated partial occlusion clamp 72 enables precise regulation of the rate of flow of the perfusion solution into the right atrium 130. The perfusion solution is concurrently pushed through line 80 through a flow sensor 82, and an integrated pressure port 84 into the left atrium 140.

The pressurised perfusion solution flowing into the aorta 150, right atrium 130, and left atrium 120 flows into the right ventricle 140, and then out through the pulmonary artery 160 into line 96 through, firstly, an integrated pressure port 90, secondly, a flow meter 92, thirdly, an afterload centrifugal pump 94 to regulate the right ventricular afterload pressure (which is measured by the flow meter 92), and finally, back into the hard-shell reservoir 20 through ingress port 28. The pressurized flow of conditioned perfusion solution into the aorta 150 via line 40 is supplied by centrifugal pump 32 and is monitored by aortic flow sensor 44. The pressurized flow of conditioned perfusion solution into the aorta 150 and then out of the pulmonary artery 160 will maintain the heart 100 in a Langendorff, isolated root perfusion state. To maintain and assess the heart's function in working mode, tight regulation of preload is required. Therefore lines 70, 80 connected to the right atrium and left atrium, respectively, comprise ⅜" tubing and receive pressurized flow of perfusion solution from the preload pump 62. Right atrial flow pressure is monitored by flow sensor 74 while left atrial flow pressure is monitored by flow sensor 82. The computer-controlled servo-actuated partial occlusion clamp 72 enables precise control over the rate of perfusion solution to the right atrium 130 and the left atrium 140, and therefore, the pressure applied to the receiving chamber. The flow meters 44, 74, 82, 92 and the integrated pressure points 46, 76, 84, 90 are connectable to and communicable with a computer for constant monitoring and integrating of the flow rates and pressures to enable constant assessment of cardiac function, i.e., the right ventricular stroke work and the left ventricular stroke work while varying resistance to the flow of perfusion solution (i.e., afterload). It should be noted that the levels of haematocrit, $Ca^{++}$, $K^+$, $NaHCO_3$, $Na^+$, $pO_2$, $CO_2$, and glucose in the perfusion solution must be balanced before perfusion starts. In the case of using bank CPD donor blood, deranged $K^+$ and $Ca^{++}$ concentrations may not allow for a homeostatic prime. This can be adjusted by haemofiltration using Ringers solution as the rinse. All these values should ideally start within normal physiological ranges and should be monitored by inline continuous blood gas analysis. The primary purpose for the perfusion solution is to avoid causing tissue edema and to maintain ion homeostasis to preserve cardiac function.

Figure 3:
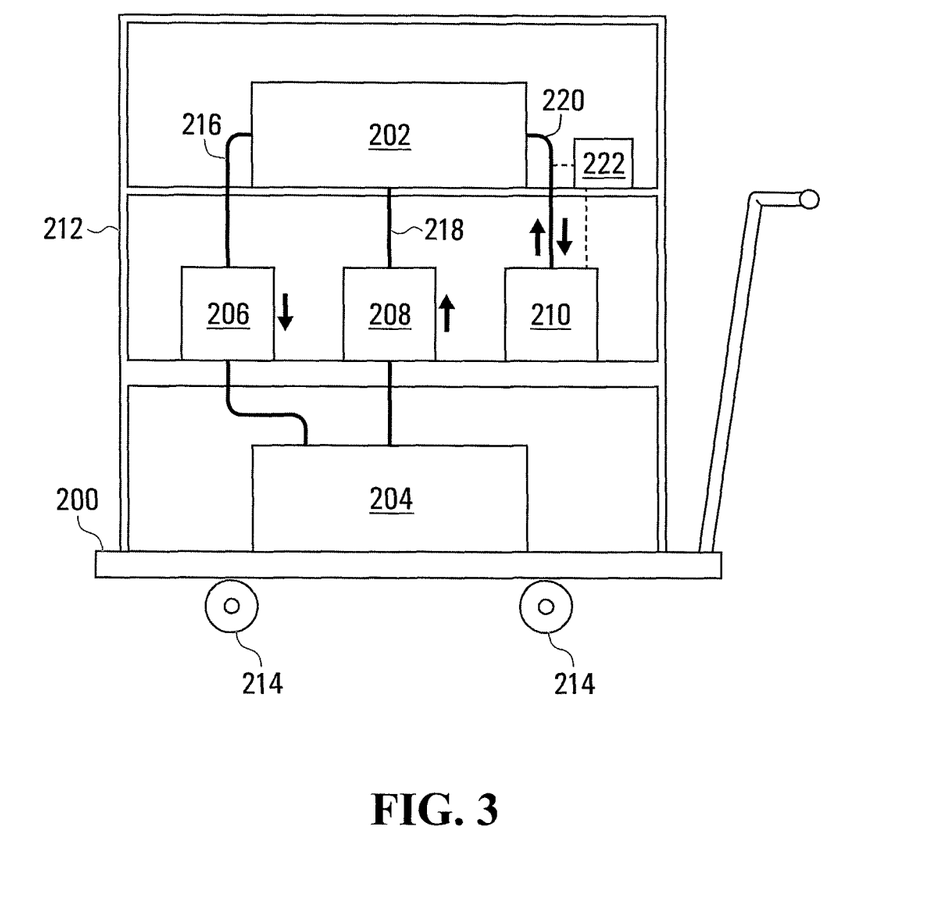
FIG. 3 is a schematic side view of a perfusion apparatus on a support, exemplary of an embodiment of the disclosure.

Another exemplary embodiment of the present disclosure relates to a support for mounting thereon and dismounting therefrom of the modules and the pumps, as illustrated in FIG. 3. As depicted in FIG. 3, a support 200 is provided for disengagably mounting thereon a first module 202, a second module 204, and pumps 206, 208 and 210. First module 202 includes the first component described above, and the second module 204 includes the second component described above. The support 200 may include a housing 212 for encasing or housing modules 202, 204 and pumps 206, 208, 210. The support 200 may be mounted on wheels 214. The modules 202, 204 are interconnected with respective conduit infrastructures 216, 218, 220, which include pumps 206, 208 and 210 respectively. Pump 206 may be similarly connected and operated as pump 32. Pump 208 may be similarly connected and operated as pump 62. Pump 210 may be similarly connected and operated as pump 94. The arrows besides pumps 206, 208 and 210 in FIG. 3 indicate the pumping directions, or the directions of the fluid pressure applied by the respective pumps, in a selected mode of operation. The support may additionally have mounts for installation of cardiac monitoring equipment and/or computer equipment and/or monitors for displaying the physiological condition and functioning of the excised heart. For example, as shown in FIG. 3, a computer 222 may be mounted on the support 200 and connected to the pumps and conduit infrastructures to control the pumps and for monitoring the conditions and functions of the excised heart. In particular, and as depicted in FIG. 3, the computer 222 may be programmed to provide computer-controlled modulation of pump 210 based on the feedback from conduit infrastructure 220. The support may be a racking system mounted on wheels so that the apparatus is transportable within a medical facility, for example between surgical theatres, staging rooms, assembly rooms and disassembly rooms. The support may be a cabinet with two opposing side walls and with other two sides having opening doors. Alternatively, the support may be a cabinet with three fixed side walls being opposing walls and having one side with opening doors. The side walls and doors may be insulated and/or cushioned. The support may be configured for transport by vehicles or by airplanes.

Another exemplary embodiment of the present disclosure relates to a system for receiving, perfusing and maintaining and assessing an excised donor heart. The system generally comprises the above-disclosed apparatus interconnected with: (i) a perfusate-processing system, (ii) a perfusate pumping system, (iii) flow sensors for monitoring the flow of perfusate to and from an installed heart's aorta, right atrium, left atrium, and pulmonary artery vena cava, (iv) an ECG apparatus interconnectable with the installed heart, (v) a pacemaker interconnectable with the installed heart, (vi) a defibrillator interconnectable with the pair of defibrillator pads integral with the inner surface of the hard-shell reservoir component of the apparatus, and (vii) probes interconnecting the installed heart with instruments for monitoring the heart's physiological functionality using load independent indices and load dependent indices. Suitable perfusion-processing systems are exemplified by heart-lung machines commonly used for coronary bypass surgeries.

An exemplary use of the apparatus, system and methods of the present disclosure generally compromises the steps of selection, preparation, and balancing of a perfusate solution, setting up the system by interconnecting the perfusate-processing system and the bi-directional perfusate pumping system with cannulae that are subsequently interconnected with the appropriate ports on the lid of the receiving, maintaining, and assessing apparatus, priming the interconnected system with the perfusate solution, installing an excised heart onto the support provided with the apparatus and then installing the appropriate cannulae into the heart's aorta, pulmonary artery, pulmonary vein, and vena cava, expressing all air from within the heart and the cannulae, and then commencing the Langendorff perfusion at a normothermic temperature from the range of about 25° C. to about 35° C.

The invention claimed is:

1. A modular perfusion apparatus for maintenance and transport of an excised donor heart, comprising:
    a first module comprising
        a hard-shell reservoir and
        a removable support in the reservoir for positioning and mounting thereon the excised heart, said hard-shell reservoir having a pair of opposing defibrillator pads engaged with an inner surface of the hard-shell reservoir;
    a second module comprising a heat-exchanger in communication with an oxygenator;
    a first conduit infrastructure interconnecting the first module, the second module and an aorta of the excised donor heart, said first conduit infrastructure having a first centrifugal pump for pushing a perfusion solution from the reservoir of the first module to the second module and from the second module to the aorta;
    a second conduit infrastructure for connecting the reservoir with a right atrium and a left atrium of the excised donor heart, said second conduit infrastructure having a second centrifugal pump for pushing the perfusion solution from the reservoir to the right atrium and the left atrium;
    a third conduit infrastructure for connecting a pulmonary artery of the excised donor heart to the reservoir, said third conduit infrastructure having a third, bi-directional centrifugal pump; and
    a computer providing computer-controlled modulation of the third pump,
    wherein the third pump is configured and the computer is programmed to modulate the third pump to provide an afterload pressure at the pulmonary artery to resist a flow of the perfusion solution from the pulmonary artery.

2. The modular perfusion apparatus of claim 1, additionally comprising a support for disengagably mounting thereon the first module, the second module, the first centrifugal pump, the second centrifugal pump, and the third centrifugal pump.

3. The modular perfusion apparatus of claim 2, wherein the support comprises a housing for the first module, the second module, the first centrifugal pump, the second centrifugal pump, and the third centrifugal pump.

4. The modular perfusion apparatus of claim 1, additionally comprising an ECG monitoring device.

5. The modular perfusion apparatus of claim 1, additionally comprising cardiac pacemaker.

6. The modular perfusion apparatus of claim 1, additionally comprising a defibrillator for communicating with the pair of defibrillator pads.

* * * * *